United States Patent
Ohtsubo et al.

(10) Patent No.: US 9,535,009 B2
(45) Date of Patent: Jan. 3, 2017

(54) INSPECTION SYSTEM

(71) Applicant: HITACHI HIGH-TECHNOLOGIES CORPORATION, Tokyo (JP)

(72) Inventors: Kenshiro Ohtsubo, Tokyo (JP); Hidetoshi Nishiyama, Tokyo (JP); Takahiro Jingu, Tokyo (JP); Masaaki Ito, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 109 days.

(21) Appl. No.: 14/401,455

(22) PCT Filed: Apr. 1, 2013

(86) PCT No.: PCT/JP2013/059817
§ 371 (c)(1),
(2) Date: Nov. 14, 2014

(87) PCT Pub. No.: WO2013/172103
PCT Pub. Date: Nov. 21, 2013

(65) Prior Publication Data
US 2015/0131087 A1 May 14, 2015

(30) Foreign Application Priority Data
May 16, 2012 (JP) .................................. 2012-112061

(51) Int. Cl.
*G01N 21/84* (2006.01)
*G01N 21/88* (2006.01)
(Continued)

(52) U.S. Cl.
CPC ...... *G01N 21/8806* (2013.01); *G01N 21/8851* (2013.01); *G01N 21/9501* (2013.01);
(Continued)

(58) Field of Classification Search
USPC .... 356/237.1–241.6, 242.1–243.8, 426–431, 356/600–640
See application file for complete search history.

(56) References Cited

U.S. PATENT DOCUMENTS 3,762,817 A * 10/1973 Harklau .................. G01N 21/55
250/226
3,781,113 A * 12/1973 Thomas ............... A61B 5/1172
250/556

(Continued)

FOREIGN PATENT DOCUMENTS

JP 2002-181726 A 6/2002
JP 2008-116405 A 5/2008

(Continued)

OTHER PUBLICATIONS

English translation of Notification of Reasons for Refusal Korean Patent Application No. 10-2014-7023940 dated Feb. 5, 2016.

(Continued)

*Primary Examiner* — Tri Ton
*Assistant Examiner* — Jarreas C Underwood
(74) *Attorney, Agent, or Firm* — McDermott Will & Emery LLP

(57) ABSTRACT

To improve sensitivity of a defect inspection, it is required to decrease influence of excessive diffraction from a spatial filter. Further, it is preferable to secure signal intensity from defects and particles as much as possible, while the influence of the excessive diffraction is decreased as much as possible. The present invention is characterized in setting a width of a spatial filter surface such that an unnecessary image caused by diffraction, that is, an intensity of the excessive diffraction is sufficiently small with respect to an intensity of a desired image. In the present invention, an SN ratio that is an index for deciding a width of the spatial filter is calculated from a region subjected to the influence of the excessive diffraction in an inspection image, and a width of a shield unit of the spatial filter is set so as to maximize the SN ratio.

14 Claims, 11 Drawing Sheets

(51) Int. Cl.
  *G01N 21/95* (2006.01)
  *G01N 21/956* (2006.01)
(52) U.S. Cl.
  CPC . *G01N 21/95623* (2013.01); *G01N 2201/068* (2013.01); *G01N 2201/06113* (2013.01); *G01N 2201/12* (2013.01)

(56) References Cited

U.S. PATENT DOCUMENTS

| | | | | |
|---|---|---|---|---|
| 4,410,278 A * | 10/1983 | Makihira | ............ | G01N 21/952 250/559.07 |
| 5,172,000 A * | 12/1992 | Scheff | ............ | G02B 27/46 250/550 |
| 5,576,829 A * | 11/1996 | Shiraishi | ............ | G01N 21/88 356/432 |
| 6,469,788 B2 * | 10/2002 | Boyd | ............ | G01N 21/211 356/369 |
| 6,608,676 B1 * | 8/2003 | Zhao | ............ | G01N 21/9501 250/559.27 |
| 6,657,714 B2 * | 12/2003 | Almogy | ............ | G01N 21/9501 356/237.3 |
| 7,106,425 B1 * | 9/2006 | Bultman | ............ | G01N 21/211 356/237.2 |
| 7,187,438 B2 * | 3/2007 | Hamamatsu | ............ | G01N 21/9501 356/237.2 |
| 7,397,557 B2 | 7/2008 | Jeong et al. | | |
| 7,733,474 B2 | 6/2010 | Aiko et al. | | |
| 8,744,167 B2 * | 6/2014 | Kang | ............ | G06T 5/002 348/42 |
| 8,764,241 B2 * | 7/2014 | Xu | ............ | G02B 27/0944 356/512 |
| 8,786,825 B2 * | 7/2014 | Van De Kerkhof | ............ | G01N 21/4788 355/53 |
| 2003/0128344 A1 * | 7/2003 | Nishi | ............ | G03F 7/70241 355/52 |
| 2006/0274305 A1 | 12/2006 | Jeong et al. | | |
| 2007/0242269 A1 * | 10/2007 | Trainer | ............ | G01N 15/0205 356/336 |
| 2009/0296096 A1 | 12/2009 | Jeong | | |
| 2011/0075151 A1 | 3/2011 | Jeong | | |
| 2013/0011043 A1 | 1/2013 | Shimura | | |
| 2013/0148116 A1 | 6/2013 | Tanaka | | |

FOREIGN PATENT DOCUMENTS

| | | |
|---|---|---|
| JP | 2008-543114 A | 11/2008 |
| JP | 2011-149869 A | 8/2011 |
| JP | 2011-523711 A | 8/2011 |
| JP | 2012-73097 A | 4/2012 |
| KR | 10-2005-0121522 A | 12/2005 |

OTHER PUBLICATIONS

International Search Report PCT/JP2013/059817 filed Jun. 18, 2013.

* cited by examiner

FIG. 4
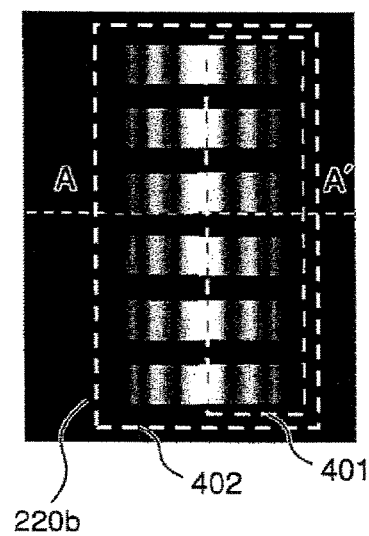
(a)
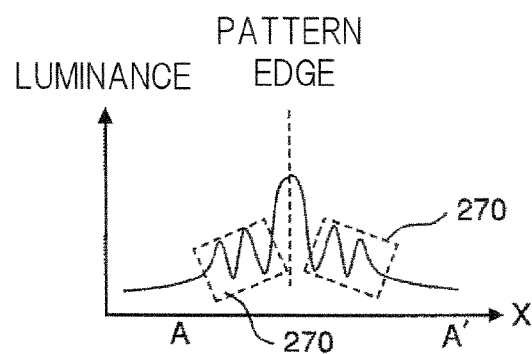
(b)

FIG. 6
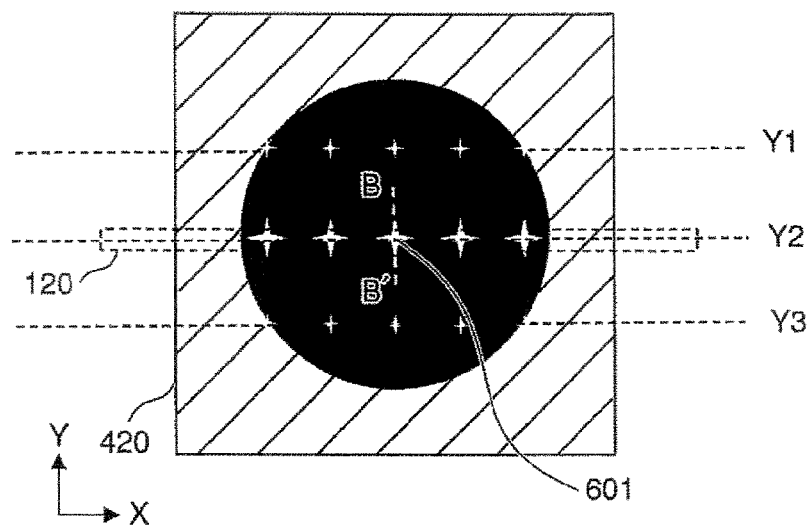
(a)
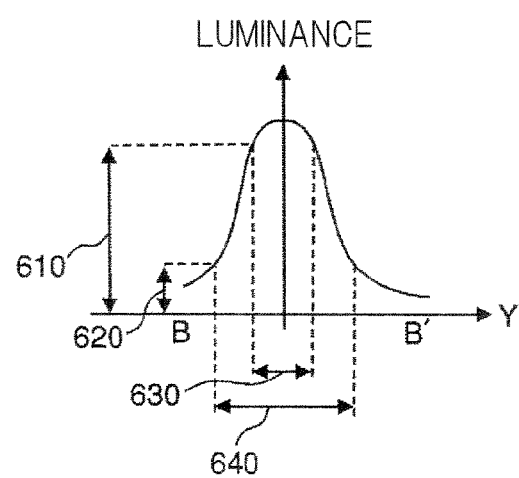
(b)

FIG. 9
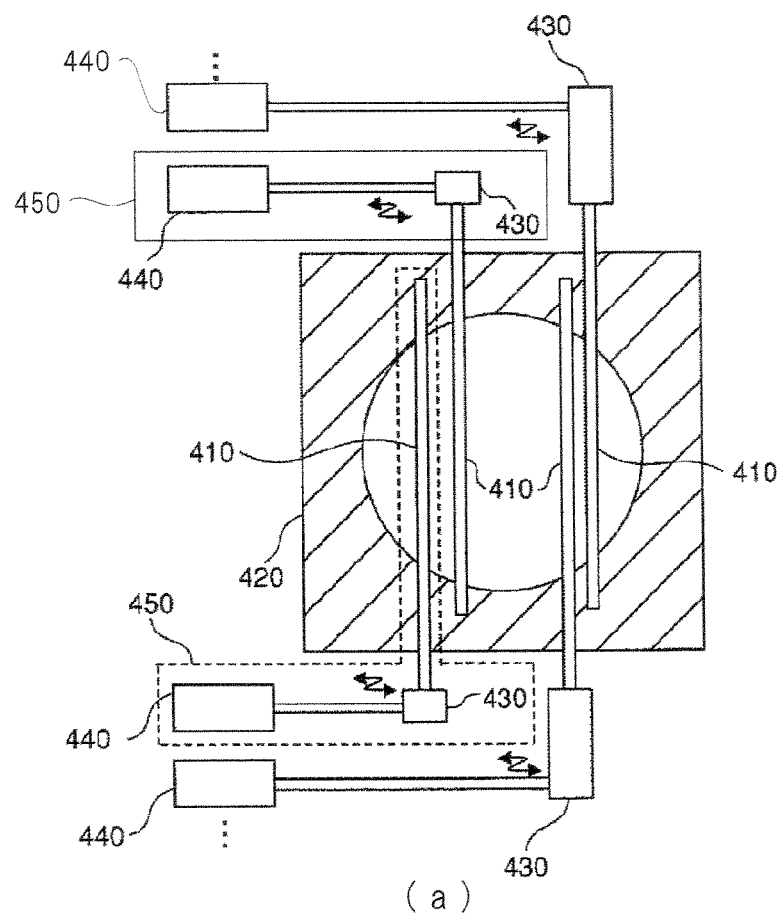
(a)
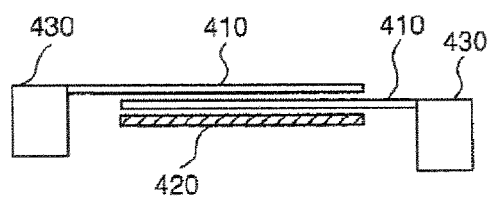
(b)
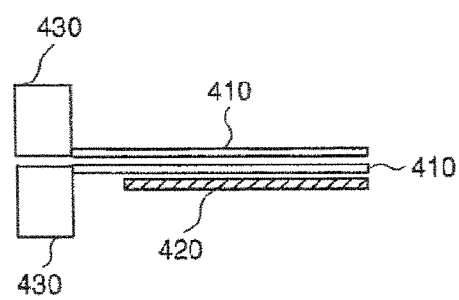
(c)

INSPECTION SYSTEM

CROSS REFERENCE TO RELATED APPLICATIONS

This application is the U.S. National Phase of PCT/JP2013/059817 filed Apr. 1, 2013, which claims priority to Japanese Patent Application No. 2012-112061 filed May 16, 2012. The subject matter of each is incorporated herein by reference in entirety.

TECHNICAL FIELD

The present invention relates to an inspection system. The present invention relates to, more particularly, an inspection system and an inspection method that detect a defect on a substrate on which a circuit pattern in a semiconductor manufacturing process is formed, and a spatial filter control apparatus and a spatial filter setting method used in the inspection system and the inspection method.

BACKGROUND ART

In a semiconductor manufacturing process, in order to promote a yield ratio, an inspection process is set in various steps during the semiconductor manufacturing process, and particles on a semiconductor substrate, defects in a formed pattern, etc. are inspected. In the semiconductor manufacturing process, fine particles on the semiconductor substrate contribute to an insulation failure of wiring and a short circuit of wiring. Along with the progress of miniaturization of patterns on semiconductor devices, minute particles on a semiconductor substrate contribute to an insulation failure of a capacitor, breakage of a gate oxide film, etc. As miniaturization of the patterns on the semiconductor devices are progressed, smaller particles or smaller defects may contribute to a failure of semiconductor devices. Therefore, an inspection system capable of detecting smaller particles and defects (they can be expressed as "defect" in some cases) on the semiconductor substrate is required.

As a technique for detecting this kind of defects on a substrate, there is known a method in which a semiconductor substrate is irradiated with laser light to detect scattering light from a particle which adheres to the semiconductor substrate or from a defect formed on the pattern. In the method, comparing an image obtained by laser irradiation with an image obtained immediately prior to the image obtained by the laser irradiation makes it possible to eliminate a false report caused by a pattern, thereby enabling a particle and a defect inspection with high sensitivity and high reliability. In addition, as the technique for inspecting a defect, there is known a method in which a wafer is irradiated with coherent light, light emitted from a repetition pattern on the wafer is removed by a spatial filter, and scattering light from a defect which does not have repetition is emphasized to be detected. Note that Patent Documents 1 to 4 are cited as prior art.

PRIOR ART DOCUMENTS

Patent Documents

Patent Document 1: U.S. Pat. No. 7,397,557
Patent Document 2: Japanese Patent Application Laid-Open Publication No. 2011-149869
Patent Document 3: Japanese Patent Application Laid-Open Publication No. 2002-181726
Patent Document 4: U.S. Pat. No. 7,733,474

DISCLOSURE OF THE INVENTION

Problems to be Solved by the Invention

Patent Document 1 discloses that undesired light is generated by a spatial filter and a light shielding plate of the spatial filter is formed in a sawtooth shape. However, it has been found in the present invention that, when an interval between the repetition patterns is decreased, in order to improve sensitivity, there is a room for improvement as to the method in Patent Document 1. It has been found in the present invention that, when the interval is decreased, the sensitivity can be improved by focusing on a width of the shielding plate of the spatial filter. In the prior art, such an idea is not taken into consideration.

Means for Solving the Problems

The present invention is characterized in setting a width of a spatial filter surface such that an unnecessary image of a spatial filter surface caused by diffraction, that is, an intensity of excessive diffraction is sufficiently small with respect to an intensity of a desired image.

In the present invention, an SN ratio that is an index for deciding a width of the spatial filter is calculated from a region influenced by the excessive diffraction in an inspection image, and a width of the spatial filter is set so as to maximize the SN ratio.

Effects of the Invention

For example, it can be expressed that the present invention has at least one of the following effects.

(1) Reducing diffraction light generated in a spatial filter edge, thereby making it possible to improve defect detection sensitivity.

(2) Capable of automatically setting a width of a spatial filter.

BRIEF DESCRIPTIONS OF THE DRAWINGS

FIG. 4 is a diagram explaining a case for capturing an image of the chip 210 illustrated in FIG. 3 by the inspection system in FIG. 1;

FIG. 6 is a diagram explaining an image of a spatial filter surface obtained by a spatial filter observation system in an observation optical system 60;

FIG. 9 is a diagram explaining a mechanism example for changing a width of the spatial filter by using a linear motor;

BEST MODE FOR CARRYING OUT THE INVENTION

Hereinafter, embodiments of the present invention will be described.

First Embodiment

Figure 1:
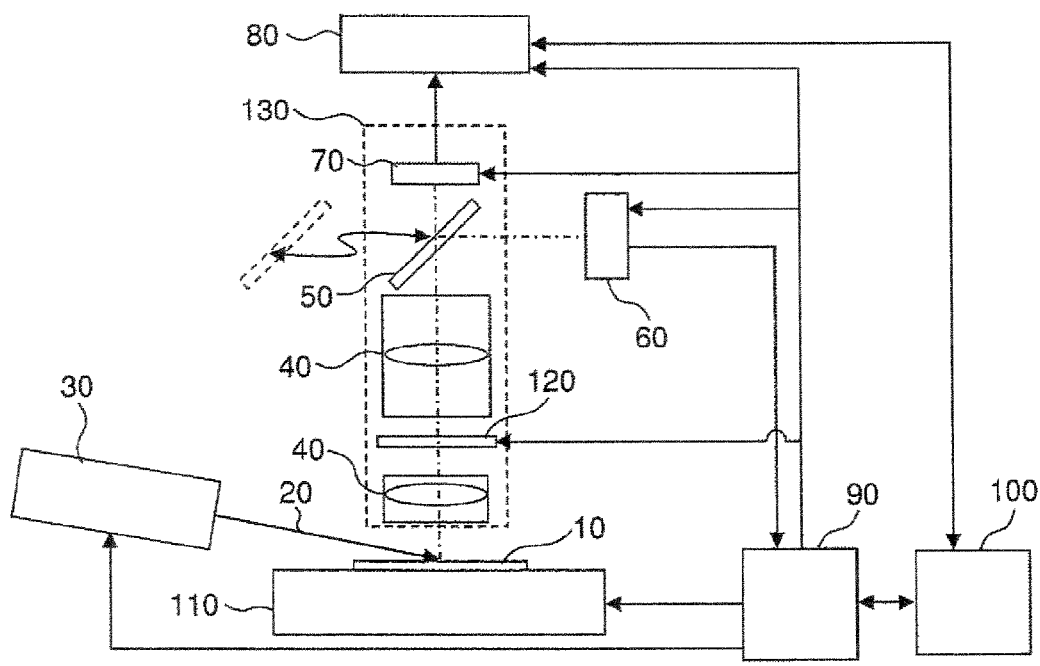
FIG. 1 is an overall block diagram of an inspection system.

FIG. 1 is an overall block diagram of an inspection system of the present embodiment. An object to be inspected 10 (such as specimen, substrate, wafer, etc.) is mounted on a stage 110. The stage 110 is configured by combining an XY stage, a Z stage, a rotating stage, etc. Although various configurations are used as the stage 110, it is preferable that the stage 110 is capable of scanning the object to be inspected 10 in an XY plane so as to enable an inspection optical system 130 installed above the stage 110 to inspect the whole surface of the object to be inspected 10.

The object to be inspected 10 is irradiated with illumination light 20 emitted from an illumination optical system 30 (including light source). Parts of scattering light from a defect (such as particle and defect in a pattern) on the object to be inspected 10 are incident on a detection lens 40, and guided into a sensor 70 through a beam splitter 50 disposed immediately before an image surface of the detection lens 40. On the other hand, the other parts of scattering light reflected by the beam splitter 50 are guided into an observation optical system 60. An inspection optical system 130 includes a spatial filter unit 120 on a spatial frequency domain inside the inspection optical system 130. The spatial filter unit 120 shields a diffraction light from a repetition pattern on the object to be inspected 10, thereby making it possible to perform inspection with high sensitivity. The light incident on the sensor 70 is photoelectrically converted into image signals, and the image signals are transmitted to an image processing unit 80. A detection lens including an analyzer may be used as the detection lens 40. A linear CCD sensor, a TDI sensor, etc. are used as the sensor 70.

The image processing unit 80 compares images captured from adjacent identical patterns, and the difference obtained from the image comparison is subjected to threshold value processing to detect a defect such as a defect. The observation optical system 60 includes an image surface observation system capable of observing an image surface of the detection lens 40, and a spatial filter observation system, capable of observing a surface of the spatial filter. The observation optical system 60 is used to set conditions of the spatial filter unit 120. The beam splitter 50 is configured to be inserted into and extracted from an optical path. In other words, the beam splitter 50 is configured to be movable, and can be disposed in and outside the optical path. Upon setting of conditions of the spatial filter unit 120, the beam splitter 50 is inserted into the optical path of the detection lens 40, and the conditions are set while images of an image surface and a spatial filter surface are observed by the observation optical system 60. In addition, at the time of inspection, the beam splitter 50 can be removed from the optical path of the detection lens 40 to prevent the influence from being exerted on the images to be captured using the sensor 70.

Figure 2:
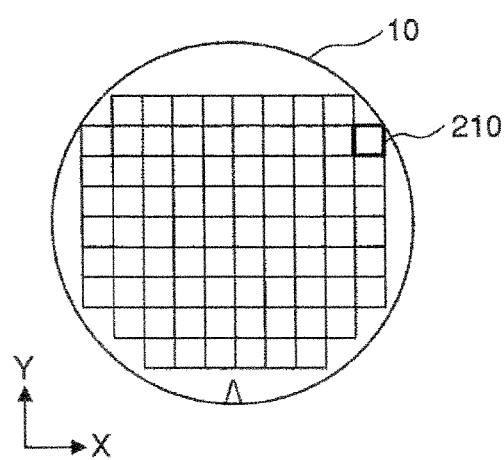
FIG. 2 is a diagram explaining an example of an object to be inspected 10.

Next, an example of the object to be inspected 10 will be described with reference to FIG. 2. In FIG. 2, the object to be inspected 10 is a disc-like semiconductor wafer in which logic LSI or memory LSI chips 210 are two-dimensionally arranged at specified interval. A surface of the object to be inspected 10 is irradiated with the illumination light 20.

Figure 3:
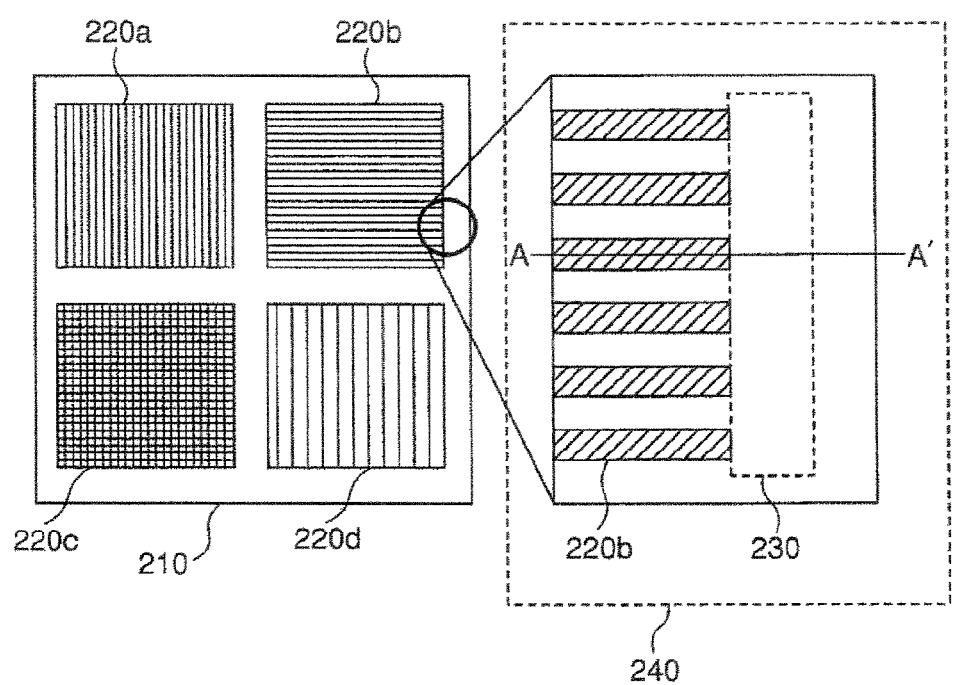
FIG. 3 is a diagram explaining the details of a chip 210 in FIG. 2.

FIG. 3 illustrates the chip 210 of FIG. 2 in detail. The chip 210 is formed mainly with memory cell regions 220a, 220b and peripheral circuit regions 220c, 220d including a decoder and a control circuit, and the chip 210 is further formed with other regions in some cases. The memory cell regions 220a, 22b are formed in a manner such that memory cell patterns, the minimum line width of which is, for example, equal to or less than 0.1 micrometers, are two-dimensionally and regularly arranged. In addition, non-repetition patterns, the minimum line width of which is, for example, equal to or less than 0.4 micrometers, are formed on the peripheral circuits 220c, 220d. That is, the region having repetition and the region not having repetition (it can be expressed that a circuit pattern is randomly formed) are present in the chip 210.

Next, a case in which an image of the chip 210 illustrated in FIG. 3 is captured by the inspection system 10 in FIG. 1 will be described with reference to FIG. 4. Among the images obtained by the censor 70 in FIG. 1, FIG. 4(a) is in particular a dark-field image of an enlarged part 240 of the pattern 220b in FIG. 3. Further, FIG. 4(b) is a luminance profile between A and A' of the dark-field image in FIG. 4(a). Note that, in FIG. 4(a) and FIG. 4(b), diffraction light generated from the repetition pattern 220b is shielded by the spatial filter unit 120. In this case, most parts of the dark-field image the pattern 220b are removed, but the image may slightly remain in a pattern edge part having a different repetition period.

Herein, a region 401 surrounded by broken lines in FIG. 4(a) corresponds to the enlarged part 240 in FIG. 3. The image should not be generated in the region 401 in FIG. 4(a) as no pattern normally is present in the enlarged part 240 in FIG. 3, but diffraction light is generated from an edge of the spatial filter unit 120, and the diffraction light is detected by the sensor 70. As a result, a stripe-like image is generated in a region 402. A luminance of the stripe-like image can be expressed as excessive diffraction 270 in FIG. 4(b), for example. Note that, as illustrated in FIG. 4(b), since the excessive diffraction 270 is generated at both the left side and the right side of the pattern edge, the excessive diffraction is observed even in the region 402 as well as outside the region 401.

Figure 5:
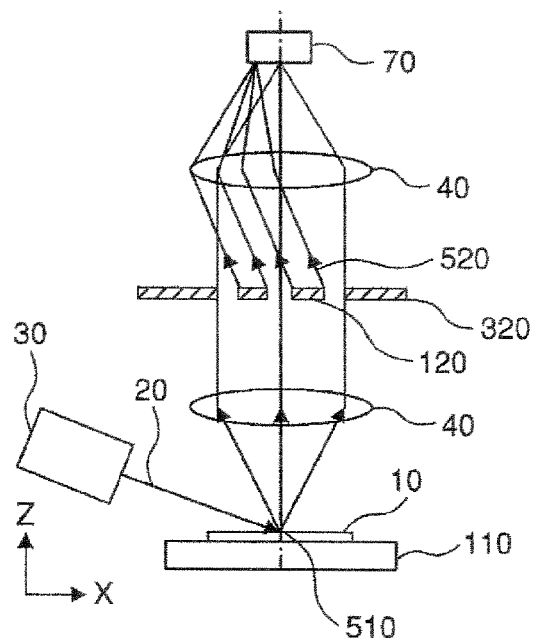
FIG. 5 is a diagram explaining a mechanism that excessive diffraction is generated from a spatial filter unit 120.

Next, the mechanism in which the excessive diffraction is generated from the spatial filter unit 120 described above will be described with reference to FIG. 1 and FIG. 5. In FIG. 1, the object to be inspected 10 is irradiated with the illumination light 20 emitted from the illumination optical system 30. Scattering light is generated from a particle 510 by the illumination light 20, and the scattering light is incident on the detection lens 40, passed through a surface of the spatial filter unit 120, and imaged to the sensor 70 through the detection lens 40.

In this case, focusing on the spatial filter, when the scattering light from the particle 510 is passed through the spatial filter unit 120, diffraction light 520 is generated from the spatial filter unit 120. It can also be expressed that the diffraction light 520 is generated, caused by overlapping of light sources in the whole aperture. Then, not only the scattering light from the particle 510, but the diffraction light 520 is also imaged on the sensor 70. This is the excessive diffraction 270 described in FIG. 4(b). When the image formed by imaging the scattering light from the particle 510 is expressed as a real image, the image formed by imaging the excessive diffraction 270 can be expressed as a virtual image. The excessive diffraction 270 is undesired light for inspection.

A magnitude of the excessive diffraction 270 is in proportion to an intensity of transmitted light near an edge part of the spatial filter unit 120. FIG. 6 is a diagram explaining an image of the spatial filter surface obtained by a spatial filter observation system in the observation optical system 60. First, a case is described in which the spatial filter unit 12 is installed with respect to an image of the spatial filter surface as in FIG. 6(*a*), so as to shield a central bright spot 601 and bright spots in parallel with the central bright spot 601 in an X direction. FIG. 6(*b*) is a luminance profile between B and B' of FIG. 6(*a*). In FIG. 6(*b*), an intensity of the transmitted light near the edge part of the spatial filter unit 120 when the spatial filter unit 120 shields light in a range 630 is higher than an intensity of the transmitted light near the edge part of a spatial filter 410 when the spatial filter 410 shields light in a range 640. That is, when a width of the spatial filter unit 120 is changed, an intensity of transmitted light near an edge part of the spatial filter unit 120 is also changed. As described above, since the magnitude of the excessive diffraction 270 is in proportion to an intensity of the transmitted light near the edge part of the spatial filter unit 120, changing the width of the spatial filter unit 120 eventually means changing the magnitude of the excessive diffraction 270.

Note that the bright spot 601 has a spread for at least one of the following reasons:

(1) A frequency of a formed repletion pattern has some widths by line edge roughness, etc.;

(2) A displacement between a position of the spatial filter unit 120 and a position of a Fourier transform surface; and (3) A relationship between a size of an irradiated region formed on a wafer by the illumination light 20 and a size of a pattern a region in an illuminated region. For example, as a SRAM memory area becomes smaller in comparison with an area of the illuminated region, the bright spot 601 has larger spread.

As described above, since the excessive diffraction 270 is undesired light for the inspection, therefore, the excessive diffraction is preferable to be as small as possible, that is, a width of the spatial filter unit 120 is preferable to be large. However, enlarging the width of the spatial filter unit 120 shows that defect signal intensity from defects and particles is also decreased because a shield area of a pupil 420 becomes large. This shows that the signal intensity from defects and particles should be ensured as much, as possible, while the excessive diffraction 270 is decreased as much as possible, so as to improve inspection sensitivity. As long as the width of the spatial filter unit 120 satisfying such a trade-off relationship is decided, an idea that the effective inspection sensitivity is likely to be improved is employed in the present embodiment.

Figure 7:
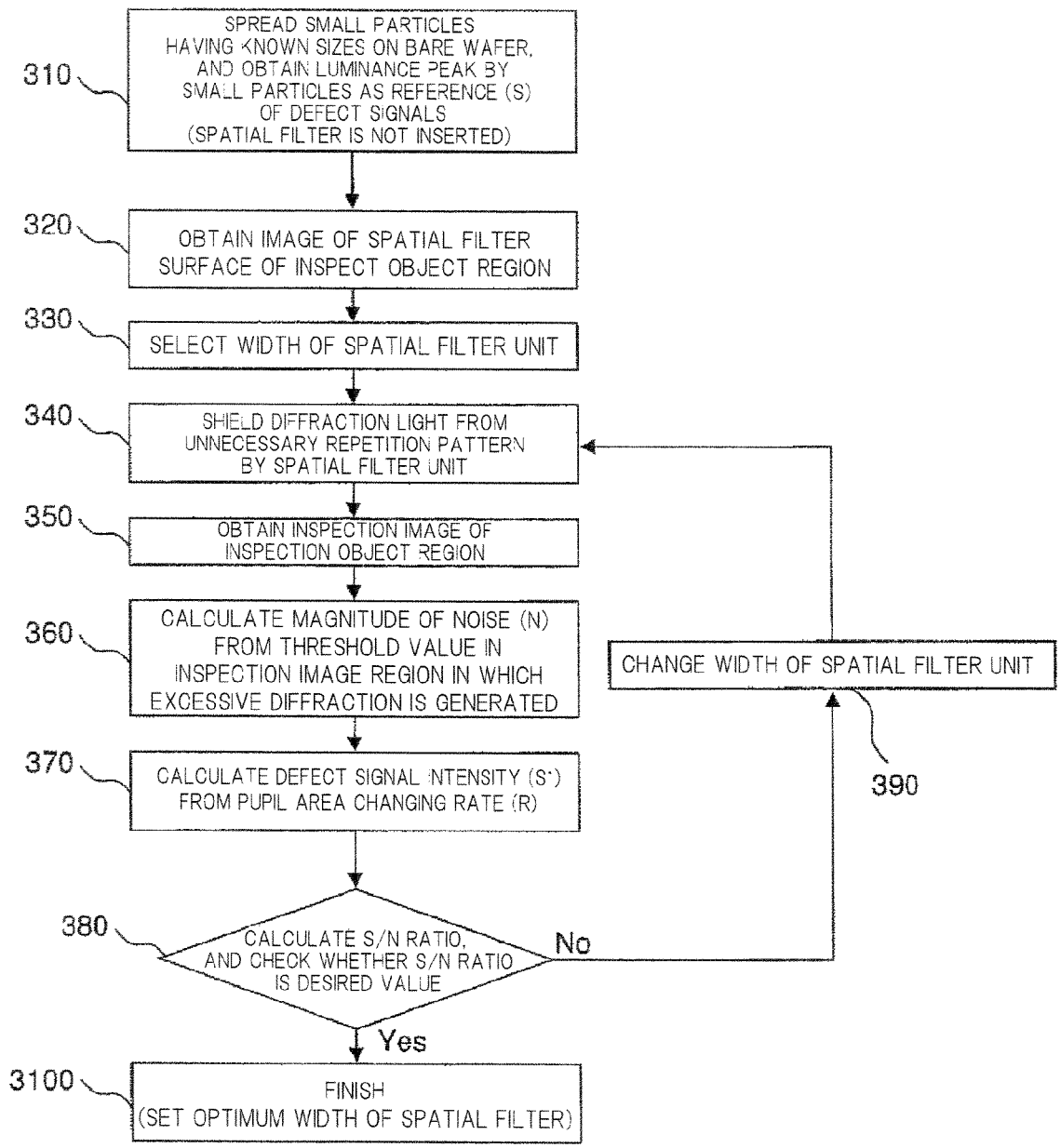
FIG. 7 is a flowchart explaining a setting method of the spatial filter unit 120.

Next, a setting method of a width of the spatial filter unit 120 will be described such that the signal intensity from defects and particles is ensured as much as possible, while the excessive diffraction 270 is decreased as much as possible as described above. FIG. 7 is a flowchart explaining a setting method of the spatial filter unit 120 in the present embodiment.

In the present embodiment, first, a bare wafer (hereinafter, it will be referred to as standard specimen) with no pattern formed is used as the object to be inspected 10, the bare wafer on which small particles (for example, standard particles such as polystyrene latex of 0.1 micrometers) having known sizes are spread. A standard specimen is mounted on the stage 110 and small particles are irradiated with the illumination light 20 from the illumination optical system 30. Scattering light from an irradiated region is detected by the detection lens 40 and received by the sensor 70. At this time, the spatial filter unit 120 is disposed outside a detection optical path of the inspection optical system 130. From an inspection image obtained in this manner, a luminance peak by the small particles is set as a reference (S) of defect signals (Step 310). Note that the reference of the defect signals is stored into a memory in a control unit 90.

Next, a wafer with a pattern to be inspected is mounted on the stage 110 as the object to be inspected 10. A region of the repetition pattern part 220*b* on the chip 210 is irradiated with the illumination light 20 from the illumination optical system 30. The scattering light from the irradiated region is detected by the spatial filter observation system in the observation optical system 60 to obtain an image of the spatial filter surface (Step 320).

An initial width of the spatial filter unit 120 is set (Step 330). As the width is changed while performing evaluation repeatedly later on, the initial width is optional, but as described later, when considering that the width of the spatial filter unit 120 is changed, setting it at a minimum or a maximum width within a setting limit is efficient.

Next, the spatial filter unit 120 is installed with an optimum position and the optimum number so as to shield diffraction light (pattern part 220*b* in this example) from an unnecessary pattern (Step 340). The optimum position and the optimum number are changed depending on conditions of the spatial filter surface. For example, in the case of an image in FIG. 6(*a*), the optimum positions are Y1, Y2 and Y3 and the optimum number is three.

Next, the beam splitter 50 is cleared from the detection optical path to obtain an inspection image by the sensor 70 (Step 350).

Next, an optional region is specified from the inspection image obtained by the sensor 70, using various input and output devices in an operation unit 100 illustrated in FIG. 1. This optional region is the region for evaluating an S/N ratio upon the inspection (for example, region 230 of FIG. 4 having a significant influence from the excessive diffraction 270). Then, noise (N) is extracted from the specified region (Step 360). Specific examples of the noise are threshold values that are preliminarily set to the region, and a standard deviation of image luminance values in the region.

Next, using the initiate width and the number of the spatial filter unit 120 which are set in step 330 and step 340, a pupil area changing rate R of the pupil 420 (set as 1 in a case of no filter) is calculated. For example, the pupil area changing rate R is a proportion of an area A1 which is capable of passing the scattering light with respect to a whole area A0 of the pupil. When an area that the pupil is occupied by the spatial filter unit 120 is set as A2, the pupil area changing rate R is expressed in the following equation.

$$R = A1/A0 = (A0 - A2)/A0$$

Then, a product of the square of the pupil aperture area changing rate R by the reference S of the defect signals described above is an amount of the scattering light passing through the pupil aperture, that is, an defect signal intensity S'. That is, the defect signal intensity S' can be expressed in the following equation. Note that the defect signal intensity S' is in proportion to the square of R due to interference of light.

$$S' = S \cdot R^2$$

As described above, S is already known as stored in the control unit 90. Further, R can also be regarded as already known by obtaining an area of the pupil, the area occupied by the spatial filter unit 120. That is, the defect signal intensity S' when the pupil area changing rate R is an optional value can be obtained in the numerical analysis by the control unit 90 or a computer additionally provided.

Moreover, with the use of small particles of the standard specimen described above, the defect signal intensity S' can be substituted by preliminarily checking a change of the defect signal intensity S' when the pupil area changing rate R is changed (Step 370). Through the steps described so far, the S/N ratio in the region for evaluating the S/N ratio can be expressed in the following equation, using S', N described above.

$$S/N \text{ ratio} = S'/N$$

Figure 8:
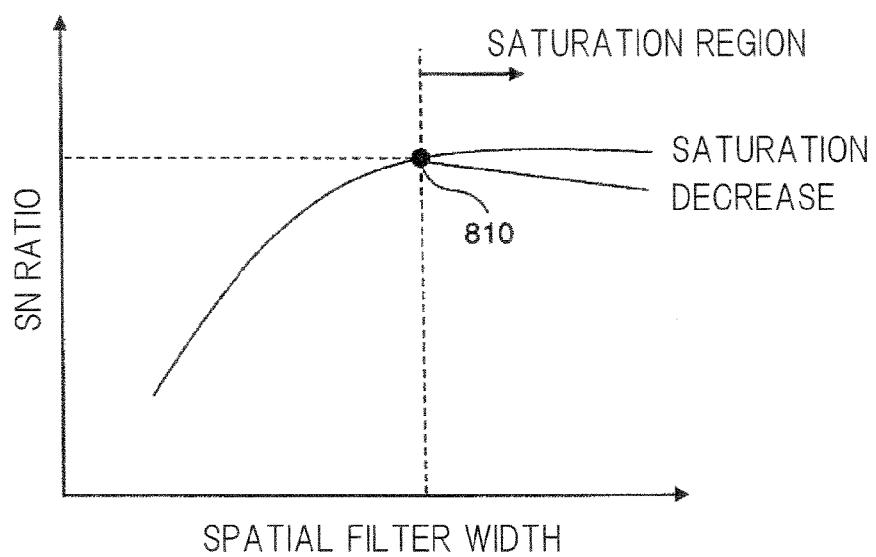
FIG. 8 is a diagram explaining a relationship between a width of the spatial filter and an S/N ratio.

Then, an operator or the control unit 90 checks whether the S/N ratio is to be a preliminarily set desired value (Step 380). If it is a desired value, the setting of the width of the spatial filter unit 120 is finished (Step 3100). The width of the spatial filter unit 120 upon performance of an actual inspection is equal to a width upon obtainment of such a desired value. Herein, the desired value can be expressed, for example, as an S/N ratio 810 upon saturation as illustrated in FIG. 8, or as a maximum value of the width of the spatial filter unit 120.

The reason for taking the saturated S/N ratio as the desired value is that the S/N ratio is saturated or decreased when exceeding a width of which the excessive diffraction is sufficiently decreased. More specifically, when there is no the excessive diffraction, the S/N ratio is saturated because S and N are decreased in the same proportion; however, since fixed noise, such as thermal noise of the sensor 70 independent of an aperture size, is practically included in N, the S/N ratio may be decreased.

Note that the desired value can be optionally changed, for example, it can be set as a value equal to or smaller than the proportion that is specified by an improvement rate of the S/N ratio. Further, when the width of the spatial filter unit 120 is spread to more than a certain degree, a decrease in the defect signals becomes significant due to a decrease in a transmission area of the Fourier transform surface. Therefore, the transmission area capable of sufficiently obtaining desired defect signals is preliminarily calculated, and a width of the spatial filter 410 that secures the transmission area can be set as a maximum value.

If the desired value is not obtained, the width of the spatial filter unit 120 is changed by the control unit 90 (Step 390), the steps from 340 to 370 are repeated until the desired value is obtained. For example, the S/N ratio can be expressed as an index for deciding the width of the spatial filter unit 120. Note that the actual inspection is performed after step 3100.

Herein, N is a value obtained from the part significantly influenced by the excessive diffraction 270, and a change of the width of the spatial filter unit 120 is reflected in the value. Further, S' is a value obtained by considering the width of the spatial filter unit 120. That is, the width of the spatial filter unit 120, when the S/N ratio described above is maximum, can be expressed as the width such that the signal intensity from defects and particles is ensured as much as possible, while the influence of the excessive diffraction 270 is decreased as much as possible. Moreover, the width of the spatial filter unit 120 can be expressed to be in a state that an intensity of the excessive diffraction is sufficiently small with respect to the signal intensity from defects and particles.

Then, since the steps described above are the process using a quantitative evaluation index (S/N ratio described above), as long as a region that evaluates the S/N ratio is specified, the other steps do not have to be decided by an operator. Therefore, the process that decides the width of the spatial filter unit 120 can be automatized by the control unit 90.

Next, a mechanism example for changing a width of the spatial filter unit 120 will be described with reference to FIG. 9. As illustrated in FIG. 9(*a*), the pupil 420 is formed on a spatial frequency domain in the inspection optical system 130. The spatial filter 410 constituted of a light shield plate composed of material such as metal is installed near above and below a surface of the pupil 420. The spatial filter 410 is fixed to a spatial filter holding unit 430, and the spatial filter holding unit 430 is connected to a linear motor actuator 440. Therefore, an installing position of the spatial filter 410 can be moved to a uniaxial direction by the operation of the linear motor actuator 440. That is, it can be expressed that a spatial filter movable unit 450 is constituted with at least one spatial filter 410, at least one spatial filter holding unit 430 and at least one linear motor actuator 440 as one set.

By installing the spatial filter movable units 450 so as to hold the pupil 420, the two spatial filters 410 can be installed on top of another such that they are slightly displaced in a vertical direction, as illustrated in FIG. 9(*b*). Further, as illustrated in FIG. 9(*c*), the spatial filters 410 can be disposed on top of another by installing the spatial filter movable units 450 in a vertical direction. As illustrated in FIG. 9(*a*), FIG. 9(*b*) and FIG. 9(*c*), it can be expressed that the spatial filter unit 120 is constituted with at least two of the spatial filters 410. In addition, it can be expressed that the operation as if the width of one spatial filter unit 120 is changed can be performed by changing the width of which the two spatial filters 410 are overlapped with each other.

Figure 10:
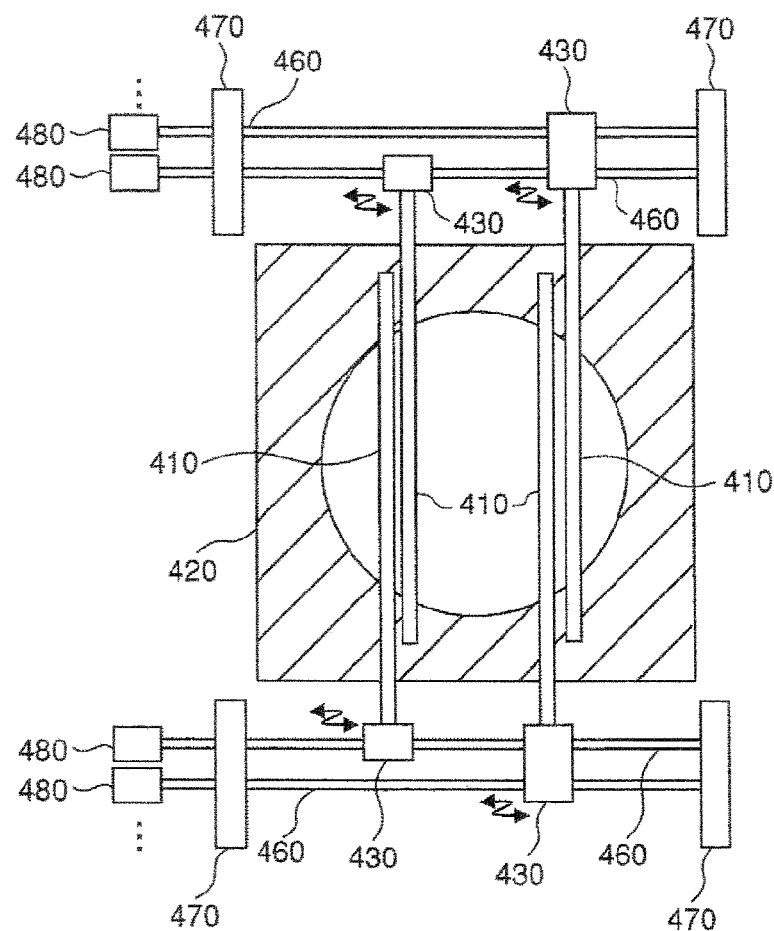
FIG. 10 is a diagram explaining a mechanism example for changing a width of the spatial filter by using a rotating motor.

Further, instead of using the linear motor actuator 440 of the spatial filter holding unit 430, as illustrated in FIG. 10, a width of the spatial filter 410 can be changed as described above, even with the configuration using ball screws 460, bearings 470 and rotating motors 480. In this case, the spatial filter supporting unit 430 is installed to the ball screw 460 through a stage guide, etc. Then, the spatial filter supporting unit 430 is horizontally moved in an axial direction of the ball screw 460 by causing the rotating motor 480 to rotate the ball screw 460, thereby making it possible for the width of the spatial filter unit 120 to be a desired value by displacing an installing position of the spatial filter 410.

Figure 11:
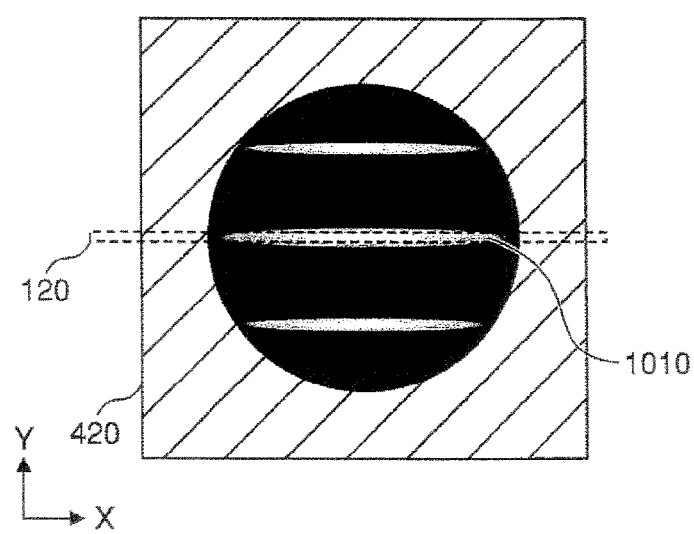
FIG. 11 is a diagram explaining a relationship between linear illumination and excessive diffraction 270.

Next, a relationship between the illumination light 20 and the excessive diffraction 270 will be described. In FIG. 1, the illumination optical system 30 can illuminate planar waves, or may include a cylindrical lens, etc. When the illumination optical system 30 includes a cylindrical lens, the illumination light 20 is lineally collected by a cylindrical lens. In this case, an image of the spatial filter surface observed by the spatial filter observation system is illustrated in FIG. 11. That is, in FIG. 11, linear diffraction light 1010 is observed, the linear diffraction light 1010 setting an X direction of the spatial filter surface as a longitudinal direction and a Y direction thereof as a lateral direction. The linear diffraction light 1010 is observed because the diffraction light from a pattern is not collected on a spatial filter surface by linearly collecting the illumination light 20, but spread in a direction where the illumination light 20 is collected. In this case, since a region having a high light intensity near an edge of the spatial filter unit 120 is larger than the case when the bright spots are scattered as in FIG. 6(*a*), the influence of the excessive diffraction 270 by the spatial filter unit 120 is more significant. This shows that the method of the present embodiment is more effective when linear illumination is formed by using a cylindrical lens, etc.

Figure 12:
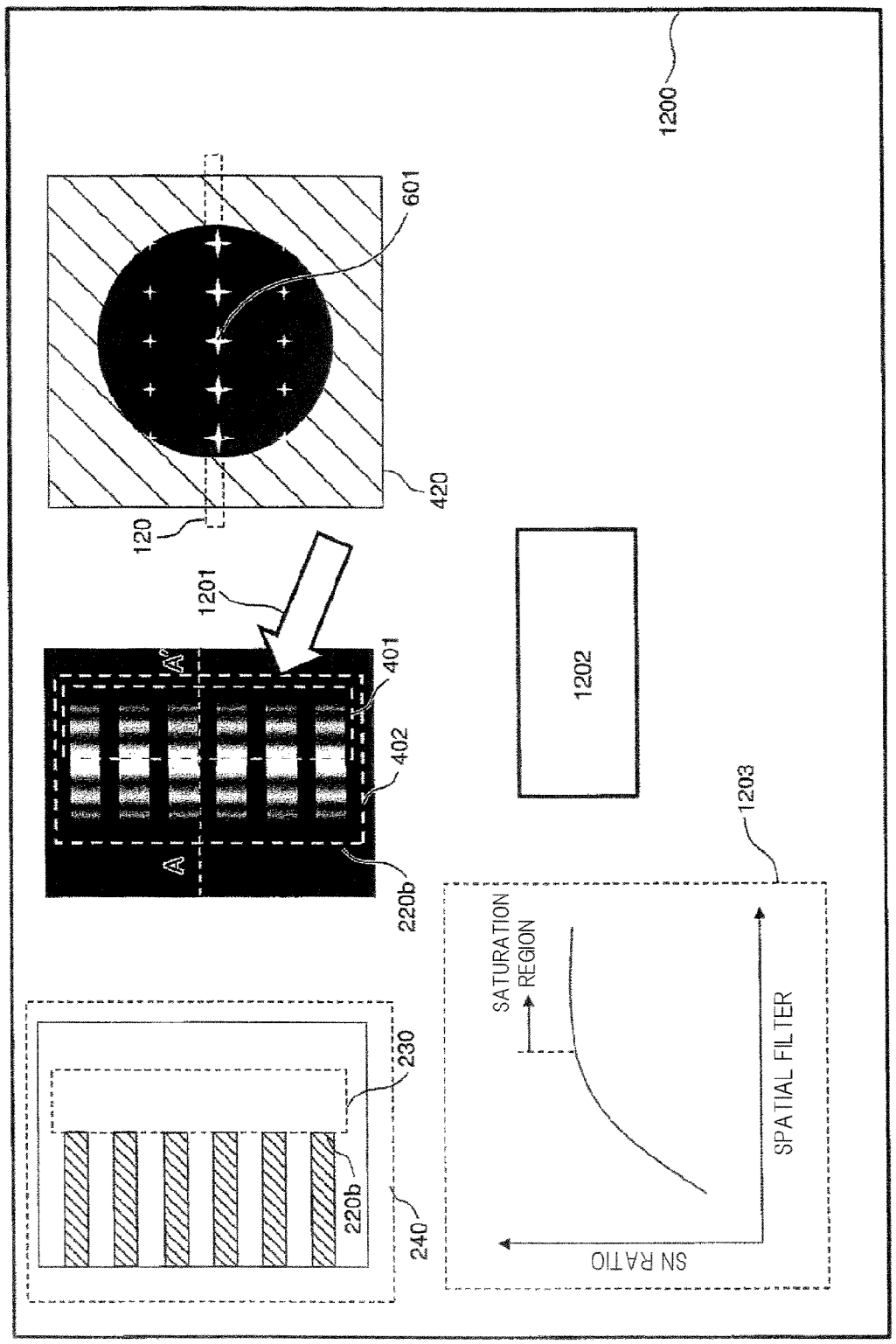
FIG. 12 is a diagram explaining a display screen.

Next, a display will be described. In the present embodiment, the setting of the spatial filter unit 120 is also possible, using a display screen 1200 illustrated in FIG. 12. In the present embodiment, for example, an image of the enlarged part 240 illustrated in FIG. 3, a dark-field image of the enlarged part 240 illustrated in FIG. 4, and an image of the spatial filter surface illustrated in FIG. 6 are displayed on the display screen 1200. Then, in specifying an optional region in step 360 of FIG. 7, the optional region is selected from the dark-field image of the enlarged part 240 by a pointer 1201 operable by an input device such as a mouse. Further, a relationship between the S/N ratio obtained by a loop from step 340 to step 390 in FIG. 7 and a width W of the spatial filter unit is illustrated as in a region 1203 surrounded by dotted lines, so that an operator can readily check that the S/N ratio becomes maximum in what width of the spatial filter unit. The setting of the width of the spatial filter unit 120 may be input through a setting window 1202. By providing the display screen described above, an operator can set the width of the spatial filter unit 120 more readily. Note that a bright-field optical system (it can be expressed as microscope) may be additionally provided so as to obtain an image of the enlarged part 240.

According to the present embodiment, since the width of the spatial filter unit 120 is decided by considering the influence of the excessive diffraction 270 and the signal intensity from defects and particles, the effective inspection sensitivity can be improved. For example, when a memory cell region such as a SRAM becomes small, a proportion of the region in which the excessive diffraction is generated to the whole inspection region is increased. That is, the present embodiment is more effective, in particular, when the interval between the repetition patterns is decreased.

Second Embodiment

Next, a second embodiment will be described. In the first embodiment, the example in which one inspection optical system 130 is used has been described. The present embodiment differs from the first embodiment in that a plurality of inspection optical systems are used. Hereinafter, the present embodiment will be described in details. In particular, the parts different from those of the first embodiment will be mainly described.

Figure 13:
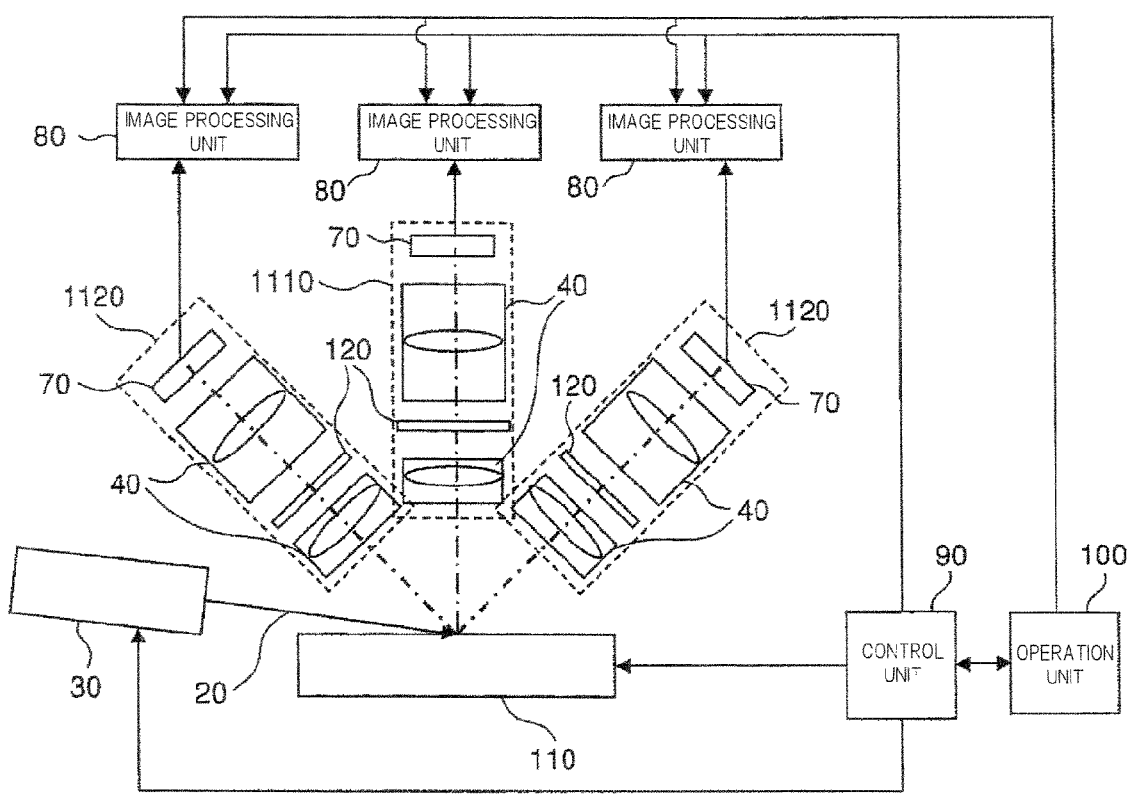
FIG. 13 is a diagram explaining a second embodiment.

FIG. 13 is a diagram explaining an inspection system of the present embodiment. The inspection system of present embodiment includes an upper inspection optical system 1110 disposed in a normal direction of the object to be inspected 10, a first oblique inspection optical system 1120 disposed at a first elevation angle with respect to the object to be inspected 10, and a second oblique inspection optical system 1130 disposed at a second elevation angle with respect to the object to be inspected 10. Each of the upper inspection optical system 1110, the first oblique inspection optical system 1120 and the second oblique inspection optical system 1130 includes the detection lenses 40, the spatial filter unit 120, and the sensor 70. Further, each of the upper inspection optical system 1110, the first oblique inspection optical system 1120 and the second oblique inspection optical system 1130 is provided with the image processing unit 80. The use of the plurality of inspection optical systems makes it possible to increase scattering lights to be collected, and to make defect decisions focusing on scattering directions of the scattering lights.

An inspection image obtained by the inspection system of the present embodiment is a dark-field image, but even when an image is captured at the same place on the object to be inspected 10, the dark-field image to be obtained differs in each of the upper inspection optical system 1110, the first oblique inspection optical system 1120 and the second oblique inspection optical system 1130. This shows that conditions of the excessive diffraction from the spatial filter unit 120, observed by each of the inspection optical systems, also differ in each of the inspection optical systems in some cases.

Therefore, in the present embodiment, the steps illustrated in FIG. 7 will be performed with respect to each of the upper inspection optical system 1110, the first oblique inspection optical system 1120 and the second oblique inspection optical system 1130, using the image processing unit 80, the control unit 90 and the operation unit 100. As described in the first embodiment, for example, the S/N ratio can be expressed as an index for deciding the width of the spatial filter unit 120, the S/N ratio that is the index is also obtained with respect to each of the inspection optical systems. This enables effective inspection sensitivity to be improved, even when the conditions of the excessive diffraction differ in each of the inspection optical systems.

As described above, the present embodiments have been described, but the present invention is not limited to the present embodiments. The present invention can be broadly applied to optical systems using a spatial filter. For example, the number of the inspection optical system is not limited to the present embodiment, employing at least two of the upper inspection optical system 1110, the first oblique inspection optical system 1120 and the second oblique inspection optical system 1130, and increasing the number of the inspection optical systems are also within a scope of the disclosure of the present specification.

Further, upon performing the inspection, the inspection system disclosed in the present embodiments is preliminarily built, and installing a program, which is stored into any storage device, capable of executing a setting method of a width of a spatial filter illustrated in FIG. 7 into the inspection system thereafter is also within a scope of disclosure of the present specification.

DESCRIPTION OF REFERENCES

10 object to be inspected
20 illumination light
30 illumination optical system
40 detection lens
50 beam splitter
60 observation optical system
70 sensor
80 image processing unit
90 control unit
100 operation unit
210 chip
120 spatial filter unit
130 inspection optical system
270 excessive diffraction
410 spatial filter
1110 upper inspection optical system
1120 first oblique inspection optical system
1130 second oblique inspection optical system

The invention claimed is:
1. An inspection system comprising:
   an illumination optical system configured to illuminate light on a substrate;
   a first detection optical system configured to form a first image by collecting and imaging light from the substrate;
   a first spatial filter configured to be inserted into and extracted from an optical path of the first detection optical system; and a processor configured to:
  obtain a first diffraction light component, which is generated from the first spatial filter when the first spatial filter is on the optical path of the first detection optical system, from the first image,
  obtain a first index for deciding a width of the first spatial filter from the first diffraction light component, and
  change a width of the spatial filter depending on the first index.

2. The inspection system according to claim 1, further comprising:
  a second detection optical system disposed at a position different from that of the first detection optical system so as to a obtain a second image; and
  a second spatial filter disposed on an optical path of the second detection optical system,
  wherein the processor is further configured to:
    obtain a second diffraction light component, which is generated from the second spatial filter, from the second image, and
    obtain a second index for deciding a width of the second spatial filter from parts including the second diffraction light component.

3. The inspection system according to claim 2,
wherein the illumination optical system forms a linear illuminated region on the substrate.

4. The inspection system according to claim 3,
wherein the first image and the second image are a dark-field image.

5. The inspection system according to claim 4,
wherein the processor is further configured to use a luminance of light obtained when the first spatial filter is outside the optical path of the first detection optical system to obtain the first index.

6. The inspection system according to claim 5,
wherein the processor is further configured to use a pupil area of the first detection optical system and an area that the pupil is occupied by the first spatial filter to obtain the first index.

7. The inspection system according to claim 6, further comprising a display configured to display an image of the first diffraction light component.

8. The inspection system according to claim 7, further comprising an input device,
wherein the processor is further configured to obtain the first index based on a range, selected from the image of the first diffraction light component, input at the input device.

9. The inspection system according to claim 1,
wherein the illumination optical system forms a linear illuminated region on the substrate.

10. The inspection system according to claim 1,
wherein the first image is a dark-field image.

11. The inspection system according to claim 1,
wherein the processor is further configured to use a luminance of light obtained when the first spatial filter is disposed outside the optical path of the first detection optical system to obtain the first index.

12. The inspection system according to claim 11,
wherein the processor is further configured to use a pupil area of the first detection optical system and an area that the pupil is occupied by the first spatial filter to obtain the first index.

13. The inspection system according to claim 1, further comprising a display configured to display an image of the first diffraction light component.

14. The inspection system according to claim 13, further comprising an input device,
wherein the processor is further configured to obtain the first index based on a range, selected from the image of the first diffraction light component, input at the input device.

* * * * *